(12) United States Patent
Robertson (10) Patent No.: US 11,865,072 B2
(45) Date of Patent: Jan. 9, 2024

(54) UNIVERSAL FLUID CONTAINER ADAPTER

(71) Applicant: Boston Scientific Scimed, Inc., Maple Grove, MN (US)

(72) Inventor: Jared Robertson, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 216 days.

(21) Appl. No.: 17/388,174

(22) Filed: Jul. 29, 2021

(65) Prior Publication Data
US 2022/0031569 A1    Feb. 3, 2022

Related U.S. Application Data

(60) Provisional application No. 63/058,150, filed on Jul. 29, 2020.

(51) Int. Cl.
*A61J 1/20* (2006.01)
*A61B 1/00* (2006.01)
*B67C 9/00* (2006.01)

(52) U.S. Cl.
CPC ......... *A61J 1/2017* (2015.05); *A61B 1/00131* (2013.01); *A61J 1/2055* (2015.05); *B67C 9/00* (2013.01)

(58) Field of Classification Search
CPC .......... A61J 1/20; A61J 1/2017; A61J 1/2055; A61B 1/00131; B67C 9/00
See application file for complete search history.

(56) References Cited

U.S. PATENT DOCUMENTS

| | | | | |
|---|---|---|---|---|
| 940,138 | A * | 11/1909 | Falls et al. ................ | B65B 1/42 141/293 |
| 1,657,783 | A * | 1/1928 | Berg ......................... | B67B 7/12 222/1 |
| 7,237,582 | B1 * | 7/2007 | Harvey .................... | B67C 11/02 141/330 |
| 7,533,701 | B2 * | 5/2009 | Gadzic .................. | B67D 1/0009 141/54 |
| 8,469,940 | B2 * | 6/2013 | Garfield ................ | A61J 1/2048 604/407 |
| 9,409,760 | B1 * | 8/2016 | Lichtefeld, Sr. .......... | B67B 7/26 |
| 10,806,667 | B2 * | 10/2020 | Denenburg ............ | A61J 1/201 |

(Continued)

FOREIGN PATENT DOCUMENTS

WO     WO-2021022127 A1 *  2/2021  ........... B09B 3/0058

*Primary Examiner* — Nicolas A Arnett
(74) *Attorney, Agent, or Firm* — Seager, Tufte & Wickhem, LLP (57) ABSTRACT

Various embodiments are generally directed to fluid container adapters that couple with a fluid container and enable different systems, such as endoscopic systems, to access the contents of the fluid container, such as via a tubing set. Several embodiments are particularly directed to a fluid container adapter that punctures a fluid container to couple with and gain access to the contents of the fluid container. In one embodiment, for example, a platform may be used to support a fluid container as one or more penetration members attached to a crossmember are advanced into the fluid container along rails connected between the platform and the crossmember. In such embodiments, the one or more penetration members may include lumens to enable a tubing set to access the contents of the fluid container.

20 Claims, 9 Drawing Sheets

(56) References Cited

U.S. PATENT DOCUMENTS

D982,399 S * 4/2023 Fritz .............................. D7/665
2013/0237761 A1* 9/2013 Cushner ............. A61B 1/00119
600/156

* cited by examiner

UNIVERSAL FLUID CONTAINER ADAPTER

PRIORITY

The present application is a non-provisional of, and claims the benefit of priority under 35 U.S.C. §119 to, U.S. Provisional Application Ser. No. 63/058,150, filed Jul. 29, 2020, the disclosures of which are herein incorporated herein by reference in their entirety.

FIELD

The present disclosure relates generally to adapters for fluid containers. In particular, the present disclosure relates to universal fluid container adapters for endoscopic systems.

BACKGROUND

Endoscopy procedures that use typical front viewing endoscopes for both therapeutic and diagnostic cases usually have some common functionalities available to an operator. One of the common functionalities includes the ability to insufflate a patient by passing a fluid, such as air or carbon dioxide, through the endoscope in a controlled manner into a target luminal space. Another of the common functionalities includes the ability to flush water across the imaging lens to clear the field of view. Yet another of the common functionalities includes the ability to irrigate the lumen to clean surfaces and aid in flushing/suctioning debris during a procedure. Oftentimes, these common functionalities, among others, are driven during a procedure by one or more fluid containers and/or sources. For example, an air pump or carbon dioxide source for insufflation, a water bottle for lens cleaning, and/or a sterile water bottle for irrigation. In some cases, a hybrid tubing set may be used to drive both lens cleaning and irrigation from a sterile water bottle. In either case, the one or more fluid containers and/or sources must be attached to the tubing set of the endoscope. It is with all of the above considerations in mind that the improvements of the present disclosure may be useful.

SUMMARY

In one aspect, the present disclosure relates to an adapter for fluid containers. The adapter for fluid containers may comprise a platform and a crossmembers. The platform may include first and second rails extending from the platform. The first and second rails may extend substantially parallel to each other. The crossmember may be slidably attached to the first and second rails such that the platform and the crossmember are substantially parallel to each other. The platform, the crossmember, and the first and second rails may be adjustable for receiving a fluid container. The crossmember may include one or more penetration members extending from the crossmember towards the platform. Each of the one or more penetration members may include a lumen and a penetrator portion with an opening to the lumen. Each of the one or more penetration members may have a penetrator portion configured for piercing the fluid container when the crossmember is moved towards the platform along the first and second rails.

In many embodiments, the opening of the penetrator portion of at least one of the one or more penetration members may comprise a plurality of radial openings to the lumen. In many such embodiments, the penetrator portion of the at least one of the one or more penetration members may comprise a conical point. In various embodiments, the penetrator portion of at least one of the one or more penetration members may comprise a beveled tip. In several embodiments, at least one of the one or more penetration members may comprise a sealing portion configured to create a seal between an exterior of the penetration member and the fluid container. In several such embodiments, the sealing portion may comprise an elastomer disposed about a circumference of the exterior surface of the penetration member.

In one or more embodiments, the first rail may comprise a first channel, the second rail may comprise a second channel, and the crossmember may comprise first and second pegs. In one or more such embodiments, the first peg may extend into the first channel to slidably attach the first rail to the crossmember and the second peg may extend into the second channel to slidably attach the second rail to the crossmember. Some embodiments may include a lever configured to slide the crossmember toward the platform along the first and second rails. In many embodiments, the lumen and the opening of at least one of the one or more penetration members are configured to have a tube extended therethrough and into an interior of the fluid container after the fluid container is pierced with the penetrator portions of the one or more penetration members.

In various embodiments, the crossmember may comprise a first side and a second side with a through hole extending from the first side to the second side, wherein at least one of the one or more penetration members extend from the first side and the through hole is in fluid communication with the lumen of the at least one penetration member. In various such embodiments, the second side may comprise a connector configured to couple the through hole to a tube and place the tube in fluid communication with the lumen of the at least one penetration member. In several embodiments, at least one of the one or more penetration members may comprise a connector portion configured to couple to a tube and place the tube in fluid communication with the lumen of the at least one penetration member. In one or more embodiments, the opening of at least one of the one or more penetration members may comprise a filter screen.

In some embodiments, the one or more penetration members may comprise a first penetration member and a second penetration member. Some such embodiments may include a pressure source in fluid communication with the lumen of the second penetration member, wherein the pressure source is configured to introduce a first fluid into an interior of the fluid container to cause a second fluid to exit the interior of the fluid container via the lumen of the first penetration member. In further such embodiments, the first penetration member may comprise a first sealing portion configured to create a seal between an exterior of the first penetration member and the fluid container, and the second penetration member may comprise a second sealing portion configured to create a seal between an exterior of the second penetration member and the fluid container.

In another aspect, the present disclosure relates to a method. The method may include attaching a first rail and a second rail to a platform. The platform may comprise a support surface configured to support a fluid container and the first and second rails may extend parallel to one another from the support surface. The method may include slidably connected a crossmember to the first and second rail. The crossmember may include one or more mounts configured to connect to one or more penetration members. The method may include connecting a penetration member to the crossmember via a mount of the one or more mounts. The penetration member may extend toward the support surface and include a lumen and a penetrator portion with an opening to the lumen. The penetrator portion may be configured to puncture the fluid container supported by the support surface and place an interior of the fluid container in fluid communication with the lumen of the penetration member via the opening when the crossmember is slid toward the support surface along the first and second rails.

In many embodiments, the method may include disposing an elastomer about an exterior circumference of the penetration member to form a sealing portion of the penetration member. In many such embodiments, the sealing portion may be configured to create a seal between the exterior of the penetration member and the fluid container when the interior of the fluid container is in fluid communication with the lumen of the penetration member. In various embodiments, the method may include inserting a first peg of the crossmember into a channel of the first rail to slidably connect the crossmember to the first rail, and inserting a second peg of the crossmember into a channel of the second rail to slidably connect the crossmember to the second rail.

In several embodiments, the method may include pivotally attaching a lever to the crossmember and configuring the lever to apply pressure to the first rail or the second rail to force the crossmember toward the support surface. In several such embodiments, the method may include extending the lever through a channel in the first rail or the second rail to configure the lever to apply pressure to the first rail or the second rail to force the crossmember toward the support surface.

In some embodiments, the method may include pivotally attaching a lever to the crossmember, wherein activation of the lever is configured to force the crossmember toward the support surface. In some such embodiments, the method may include extending the lever through a channel in the first rail or the second rail to configure the lever to force the crossmember toward the support surface.

In yet another aspect, the present disclosure relates to an apparatus comprising a platform, a first rail, a second rail, a crossmember, and a penetration member. The platform may comprise a support surface configured to support a fluid container. The first rail may be attached to the platform and extend from the support surface. The second rail may be attached to the platform and extend from the support surface parallel to the first rail. The crossmember may be slidably connected to the first and second rail. The crossmember may include one or more mounts configured to connect to one or more penetration members. The penetration member may be connected to the crossmember via a mount of the one or more mounts and extend toward the support surface. The penetration member may include a lumen and a penetrator portion with an opening to the lumen. The penetrator portion may be configured to puncture the fluid container supported by the support surface and place an interior of the fluid container in fluid communication with the lumen of the penetration member via the opening when the crossmember is slid toward the support surface along the first and second rails.

In many embodiments, the opening of the penetrator portion may comprise a plurality of radial openings to the lumen. In many such embodiments, the penetrator portion may comprise a conical point. In various embodiments, the penetrator portion may comprise a beveled tip at the opening. In several embodiments, the penetration member may comprise a sealing portion configured to create a seal between an exterior of the penetration member and the fluid container when the interior of the fluid container is in fluid communication with the lumen of the penetration member. In several such embodiments, the sealing portion may comprise an elastomer disposed about a circumference of the exterior surface of the penetration member.

In one or more embodiments, the first rail may comprise a first channel, the second rail may comprise a second channel, and the crossmember may comprise first and second pegs. In one or more such embodiments, the first peg may extend into the first channel to slidably connect the first rail to the crossmember and the second peg may extend into the second channel to slidably connect the second rail to the crossmember. Some embodiments may include a lever configured to slide the crossmember toward the support surface along the first and second rails. In many embodiments, the lumen and the opening of the penetration member are configured to have a tube extended therethrough and into the interior of the fluid container when the interior of the fluid container is in fluid communication with the lumen of the penetration member via the opening.

In various embodiments, the crossmember may comprise a first side and a second side with a through hole extending from the first side to the second side, wherein the first side includes the mount and the through hole is in fluid communication with the lumen of the penetration member. In various such embodiments, the second side may comprise a connector configured to couple the through hole to a tube and place the tube in fluid communication with the lumen of the penetration member. In several embodiments, the penetration member may comprise a connector portion configured to couple to a tube and place the tube in fluid communication with the lumen of the penetration member. In one or more embodiments, the opening may include a filter screen.

In some embodiments, the penetration member may comprise a first penetration member. Some such embodiments may include a second penetration member connected to the crossmember via a second mount of the one or more mounts and extending toward the support surface. The second penetration member may comprise a second lumen and a second penetrator portion with at least one opening to the second lumen. The second penetrator portion may be configured to puncture the fluid container supported by the support surface and place and interior of the fluid container in fluid communication with the second lumen of the second penetration member via the at least one opening when the crossmember is slid toward the support surface along the first and second rails. Further such embodiments may include a pressure source in fluid communication with the second lumen, and the pressure source may be configured to introduce a first fluid into the interior of the fluid container to cause a second fluid to exit the interior of the fluid container via the first penetration member. In still further embodiments, the first penetration member may comprise a first sealing portion configured to create a seal between an exterior of the first penetration member and the fluid container, and the second penetration member may comprise a second sealing portion configured to create a seal between an exterior of the second penetration member and the fluid container.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Various embodiments are generally directed to fluid container adapters that couple with a fluid container, so to enable access to the contents of the fluid container, such as from an endoscopic system via a tubing set. Several embodiments are particularly directed to a fluid container adapter that punctures a fluid container to couple with and gain access to the contents of the fluid container. In one embodiment, for example, a platform may be used to support a fluid container as one or more penetration members attached to a crossmember are advanced into the fluid container along rails connected between the platform and the crossmember. In such embodiments, the one or more penetration members may include lumens to enable a tubing set to access the contents of the fluid container. These and other embodiments are described and claimed.

Some challenges in coupling with a fluid container and gaining access to the contents of the fluid container include having a fluid container adapter that is compatible with the fluid container. For example, a fluid container adapter may include a screw cap with one or more tubes extending therethrough. In such examples, the screw cap may couple to corresponding threads on a neck of the fluid container with the one or more tubes extending therethrough enabling the endoscopic system to access the contents of the fluid container. However, there are many different types of fluid container manufacturers that offer different fluid container designs. Further, manufacturers may offer different fluid container designs and/or periodically change or update fluid container designs. For instance, manufacturers may offer designs with different thread patterns around the world based on regional preferences or demands. This presents a challenge for manufacturers of tubing sets by requiring them to offer multiple products with customized fluid container adapters for each design. Further, product acquisition and stocking by health care facilities is complicated by necessitating they ensure that tubing sets have a fluid container adapter that is compatible with an available fluid container.

Accordingly, various embodiments of the present disclosure include fluid container adapters that widen the scope of compatibility to a variety of different fluid container designs. In many embodiments, one or more fluid container adapters of the present disclosure may provide an efficient, safe, and effective way to couple with and gain access to the contents of a multitude of fluid container designs. Enabling fluid container adapters to be compatible with different fluid container designs allows manufacturers of tubing sets to offer products that are more adaptable and appeal to a broader market. Further, enabling fluid container adapters to be compatible with different fluid container designs can simplify product acquisition and stocking by health care facilities.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Although endoscopes and endoscopic systems are referenced herein, reference to endoscopes, endoscopic systems, or endoscopy should not be construed as limiting the possible applications of the disclosed aspects. For example, the disclosed aspects may be used in conjunction with duodenoscopes, bronchoscopes, ureteroscopes, colonoscopes, catheters, diagnostic or therapeutic tools or devices, or other types of medical devices or systems.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

Figure 1:
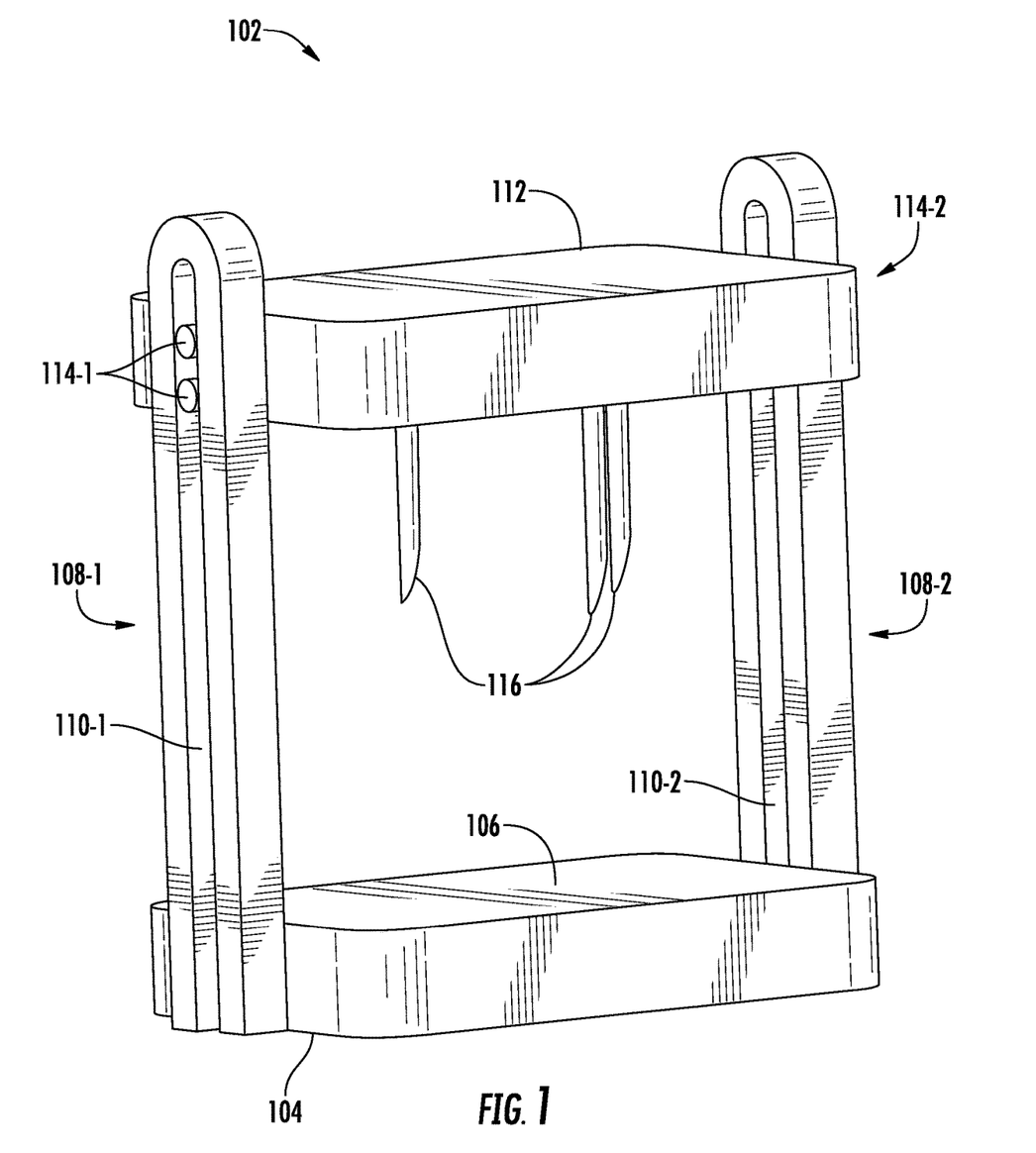
FIG. 1 illustrates various aspects of a fluid container adapter according to one or more embodiments of the present disclosure.

FIG. 1 illustrates various aspects of a fluid container adapter 102 according to one or more embodiments of the present disclosure. In some embodiments, FIG. 1 may include one or more components that are the same or similar to one or more other components of the present disclosure. Further, one or more components of FIG. 1, or aspects thereof, may be incorporated into other embodiments of the present disclosure without departing from the scope of this disclosure. In the illustrated embodiment, fluid container adapter 102 includes a platform 104, rails 108-1, 108-2 (or rails 108), and crossmember 112. Platform 104 includes a support surface 106, rail 108-1 includes a channel 110-1, rail 108-2 includes a channel 110-2, and crossmember 112 includes pegs 114-1, 114-2 (or pegs 114) and penetration members 116. In one or more embodiments of the present disclosure, the components of fluid container adapter 102 may interoperate to couple with a fluid container and enable an endoscopic system to access the contents of the fluid container. Embodiments are not limited in this context.

The platform 104 may be arranged to receive or support a fluid container. For example, a fluid container may be placed on the support surface 106 of platform 104 between the rails 108 and under crossmember 112. The rails 108 may extend between the platform 104 and the crossmember 112. For instance, rails 108 may extend, parallel to one another, from the support surface 106 to the crossmember 112. The rails 108 may connect to platform 104 and the crossmember 112. One or more of these connections are configured to allow movement of at least one of the platform 104 and the crossmember 112 relative to one another. Further, the movement of at least one of the platform 104 and the crossmember 112 relative to one another enables penetration members 116 to puncture a fluid container placed on the support surface 106.

It will be appreciated that although fluid container adapter 102 is illustrated with three penetration members 116, any number of penetration members could be used without departing from the scope of this disclosure. Penetration member 116 may be a hollow elongate tubular body, attached at one end to the crossmember 112 and extending substantially perpendicular away from the crossmember 112. In some embodiments, a tip of penetration member 116 may be sharpened or pointed. Penetration members 116 may be configured to puncture or pierce through a surface of a fluid container for delivering and/or removing fluid from within the fluid container. Penetration members, along with exemplary embodiments, are described in more detail below, such as with respect to FIGS. 4-6. In one or more embodiments, fluid container adapter 102 may include one or more valves (e.g., one-way vales, pressure relief vales, two-way valves, and the like) to control the flow of fluids into and/or out of a fluid container. For example, a one-way valve may be utilized to prevent back flow into a fluid container.

In the illustrated embodiment, the connection between rails 108 and platform 104 may be a static connection and the connection between rails 108 and crossmember 112 may be a slidable connection. In other words, the connections between platform 104 and rails 108 may provide zero degrees of freedom while the connections between crossmember 112 and rails 108 may provide one degree of freedom. For example, the slidable connection between crossmember 112 and rails 108 may allow the crossmember 112 to displace away from the platform 104 to enable a fluid container to be loaded onto the support surface 106 between the support surface 106 and the penetration members extending from the crossmember 112. Further, once the fluid container is loaded onto the support surface 106, the slidable connection between crossmember 112 and rails 108 may allow the crossmember 112 to displace toward the platform 104 and cause penetration members 116 to puncture the fluid container. In some embodiments, the platform 104 may include one or more penetration members extending towards the crossmember 112.

In other embodiments, the platform 104 and the crossmember 112 may be slidably attached to the rails. In yet another embodiment, the platform 104 may be slidably attached to the rails 108 and the crossmember 112 may be statically connected to the rails 108. In still another embodiment, the platform 104 and the crossmember 112 may be statically connected to the rails 108. For example, the rails 108 may be telescoping to allow movement of the platform 104 and crossmember 112 relative to each other. In various embodiments, crossmember 112 and/or platform 104 may include channels, slots, or through holes to connect to rails 108. For example, crossmember 112 may include one or more through holes that each of the rails 108 extend through to provide a slidable connection between the crossmember 112 and the rails 108. Additionally, or alternatively, rail 108-1 may include a slot that peg 114-1 extends into and rail 108-2 may include a slot that peg 114-2 extends into to establish a slidable connection between the cross member 112 and the rails 108.

Referring back to the illustrated embodiment, pegs 114-1 may extend from crossmember 112 into the channel 110-1 of rail 108-1 to provide a slidable connection between rail 108-1 and crossmember 112. Similarly, pegs 114-2 may extend from crossmember 112 into the channel 110-2 of rail 108-2 to provide a slidable connection between rail 108-1 and crossmember 112. In other embodiments, each of the connections between crossmember 112 and rails 108 and/or between platform 104 and rails 108 may provide one or more degrees of freedom. For example, only a single peg may extend from crossmember 112 into the channels 110 of rails 108 to provide both linear and rotational degrees of freedom between crossmember 112 and rails 108. In some embodiments, pegs 114 are integrally formed with the crossmember 112. In other embodiments, the pegs 114 are attached to the crossmember 112. For example, the crossmember 112 may include threaded holes that pegs 114 screw into. In embodiments in which the platform 104 is slidably connected to the rails 110, the platform 104 may be attached to the rails 110 in the same or similar manner as described with respect to crossmember 112.

In some embodiments, the different connections may provide different degrees of freedom. For example, the different degrees of freedom may be orthogonal to one another. In another example, connections between the rails 108 and the crossmember 112 may provide a rotational degree of freedom and connections between the rails 108 and the platform 104 may provide a linear degree of freedom. In several embodiments, a combination of various degrees of freedom in one or more connections may allow the penetration members 116 to be placed in a desired orientation with respect to a fluid container.

In several embodiments, motion in one or more of the degrees of freedom may be mediated and/or restricted. For example, a slight interference fit between the channels 110 and pegs 114 may allow the crossmember 112 to remain in a position relative to the platform 104 in the absence of an external force other than gravity. In various embodiments, by mediating and/or restricting motion in one or more degrees of freedom, a fluid container may be placed between the platform 104 and the crossmember 112 without having to actively support the crossmember 112.

In some embodiments, motion in one or more of the degrees may be mediated and/or restricted via a locking mechanism. In some such embodiments, a locking mechanism may lock movement of one or more of the platform 104 and the crossmember 112 in position at one or more extents of a range in a degree of freedom. For example, a first locking member may restrict motion of the crossmember 112 to enable loading of a fluid container and/or a second locking member may restrict motion of the crossmember 112 to prevent unintended exposure to a penetration member, such as by locking the penetration members 116 against support surface 106 for transport and/or storage. In some such examples, platform 104 may include corresponding recesses that each penetration member extends into when the second locking member is engaged.

In one or more embodiments, the connections may comprise one or more actuators or machines, such as a linear actuator and or simple machine (e.g., rack and pinion, screw jack, lever, or the like). In one or more such embodiments, the one or more actuators may provide assist in forcing the penetration members 116 to puncture a fluid container. In various embodiments, a lever may be pivotally attached to the crossmember. In various such embodiments, activation of the lever is configured to force the crossmember toward the support surface. For instance, a lever may extend through channel 110-1 above crossmember 112 and be used to force crossmember 112 toward support surface 106. In some such instances, the lever may apply pressure to the first rail or the second rail to force the crossmember toward the support surface. In many embodiments, one or more connections may be formed using various techniques, such as welding, adhesives, screws, molding, and the like. In some embodiments, one or more connections may be integrally formed with one or more components. For instance, rails 108 may be integrally formed with platform 104 or welded to platform 104.

A variety of materials may be used in the fluid container adapter 102. In some embodiments, the rigid components of fluid container adapter 102 (e.g., platform 104, rails 108, crossmember 112, pegs 114, and penetration members 116) may be constructed from one or more of metal, composites, plastics, and the like. For example, platform 104, crossmember 112, and pegs 114 may comprise a plastic or composite material while rails 108 and penetration members 116 comprise a metal. In several embodiments, the penetration members 116 may comprise a material that facilitates a sharpened tip (e.g., penetrator), such as metal or ceramic. In many embodiments, components of fluid container adapter 102 may include antimicrobial surfaces and/or materials.

In several embodiments, a method for utilizing the fluid container adapter 102 may proceed with one or more of the following steps. A first end of one or more tubes may be connected to an endoscopic device or system and a second end of the one or more tubes may be placed in fluid communication with the one or more penetration members 116, such as by connecting each tube to a separate penetration members. A fluid container may be loaded onto the support surface 106 of the platform 104 below the penetration members 116. The crossmember 112 may then be forced towards the support surface 106 (e.g., via a linear actuator), causing the penetration members 116 to pierce the fluid container and place each of the one or more tubes in fluid communication with the interior of the fluid container. Oftentimes, a first tube of the one or more tubes may be placed in fluid communication with a first fluid (e.g., a gas) in the interior of the fluid container and a second tube of the one or more tubes may be placed in fluid communication with a second fluid (e.g., a liquid) in the interior of the fluid container.

Figure 2A:
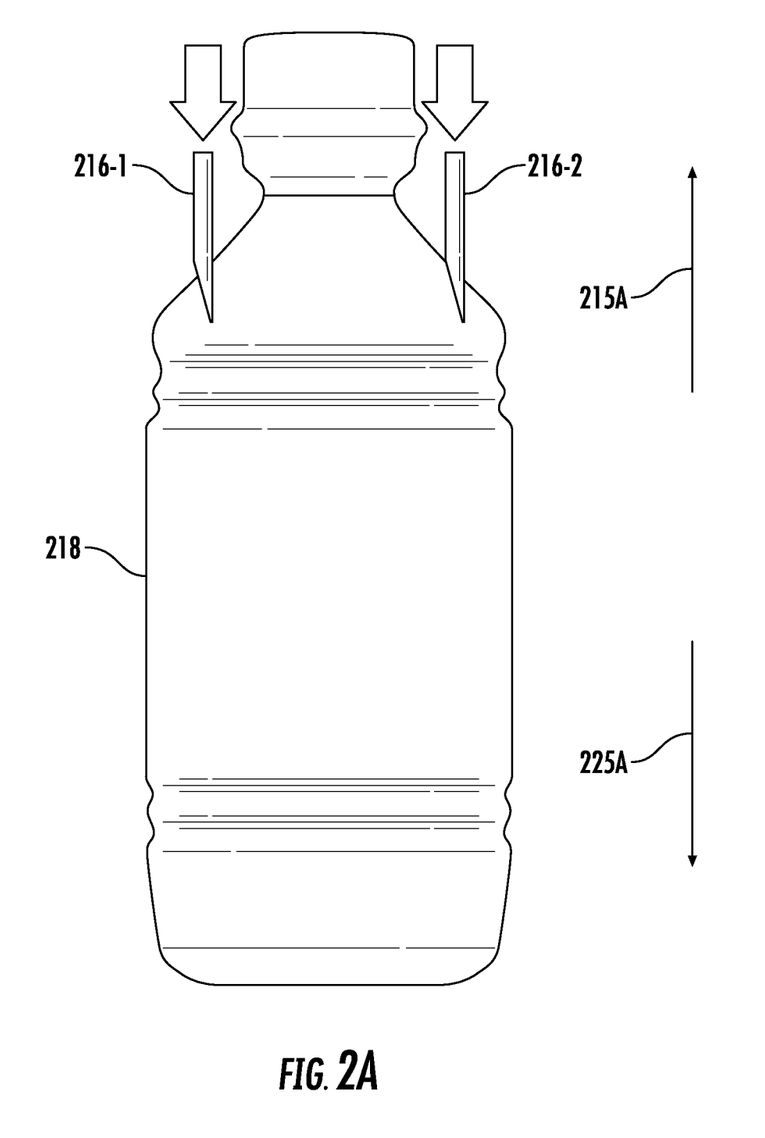
FIG. 2A illustrates various aspects of penetration members in conjunction with a fluid container in a first orientation according to one or more embodiments of the present disclosure.
Figure 2B:
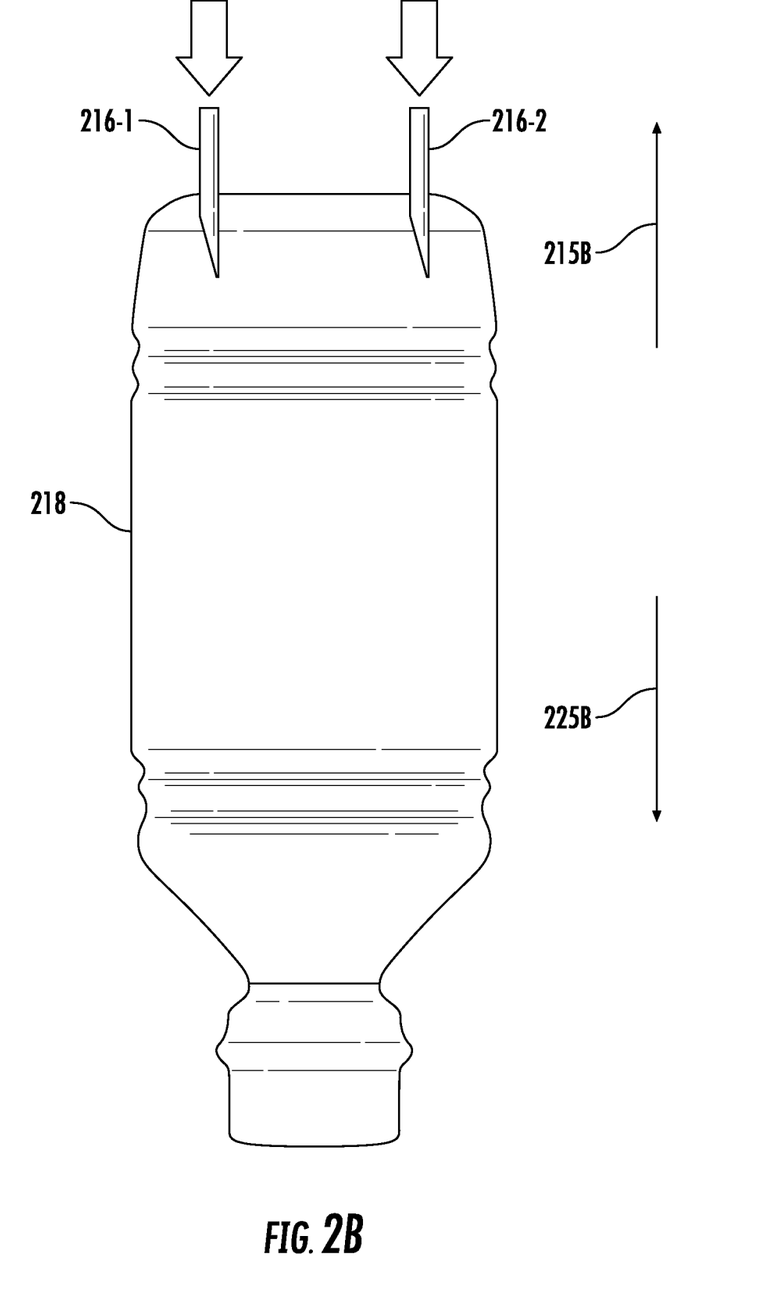
FIG. 2B illustrates various aspects of penetration members in conjunction with a fluid container in a second orientation according to one or more embodiments of the present disclosure.

FIGS. 2A and 2B illustrate various aspects of penetration members in conjunction with a fluid container in according to one or more embodiments of the present disclosure. More specifically, FIG. 2A illustrates penetration members 216-1, 216-2 (or penetration members 216) in conjunction with fluid container 218 in a first orientation with top 215A and bottom 225A and FIG. 2B illustrates penetration members 216-1, 216-2 (or penetration members 216) in conjunction with fluid container 218 in a first orientation with top 215B and bottom 225B. In some embodiments, FIGS. 2A and/or 2B may include one or more components that are the same or similar to one or more other components of the present disclosure. Further, one or more components of FIGS. 2A and/or 2B, or aspects thereof, may be incorporated into other embodiments of the present disclosure without departing from the scope of this disclosure. For example, penetration member 216 may be incorporated into fluid container adapter 102 as penetration members 116. In each orientation the support surface (e.g., support surface 106) of the fluid container adapter (e.g., fluid container adapter 102) contacts the fluid container 218 proximate the bottoms 225A, 225B and the penetration members 216 puncture the fluid container proximate the tops 215A, 215B. In some embodiments, the support surface may include one or more features to receive the bottoms 225A, 225B. For example, support surface 106 may include an opening to receive the bottom 225B of fluid container 218. Embodiments are not limited in this context.

In various embodiments, the penetration members 216 may be used to remove fluids from and/or introduce fluids into the interior of the fluid container 218. For example, penetration member 216-1 may be used to pump a gas (e.g., air, carbon dioxide, etc.) into the fluid container 218 and penetration member 216-2 may allow a liquid (e.g., water, saline, etc.) to exit the fluid container 218 as a result of the air being pumped into the fluid container 218. In another example, penetration member 216-1 may be used to suck a liquid out of the fluid container 218 and penetration member 216-2 may allow gas pressure in the fluid container 218 to equalize with the atmosphere. In such other examples, a one-way valve and/or a pressure relief valve may be utilized to equalize with the atmosphere. In various embodiments, the liquid may be sucked or forced into a tube comprising an irrigation line. It is also understood that penetration members 116 may be extended any length into the fluid container 218. For example, the penetration members 116 may extend to but not penetrate or pierce through the bottoms 225A, 225B.

In various embodiments, the penetration members may have different lengths and/or extend into fluid container 218 different lengths. For example, a shorter penetration member may allow a gas to be pumped into the fluid container 218 without introducing bubbles into a liquid and a longer penetration member may extend into the liquid and enable the introduced gas to force the liquid out of the fluid container 218 via the longer penetration member. In another example, neither of the penetration members may extend into the liquid, instead a tube may be inserted through and extended into the liquid. In some embodiments a tube may be inserted through a penetration member and extended into the liquid to keep the input submerged and reduce or prevent a gas from being introduced into the tube before the fluid container 218 is empty.

It will be appreciated that other orientations are possible without departing from the scope of this disclosure. In some embodiments, penetration members 216 could penetrate an opposite end as depicted in FIGS. 2A and 2B, or a side of the fluid container. For example, penetration members 216 could access the interior of fluid container 218 via bottom 225A in FIG. 2A or bottom 225B in FIG. 2B. In such examples, the penetration members 216 may extend from a support surface of a fluid container adapter (see e.g., support surface 106 of fluid container adapter 102). Further, in some embodiments, one or more of the penetration members may be coaxial. For example, a first penetration member may be disposed coaxially with a second penetration member having a larger diameter, resulting in inner and outer penetration members. In some such examples, the inner penetration member may not include a penetrator portion. Similarly, in such examples, the tubes connecting to the first and second penetration members may be coaxial.

Figure 3A:
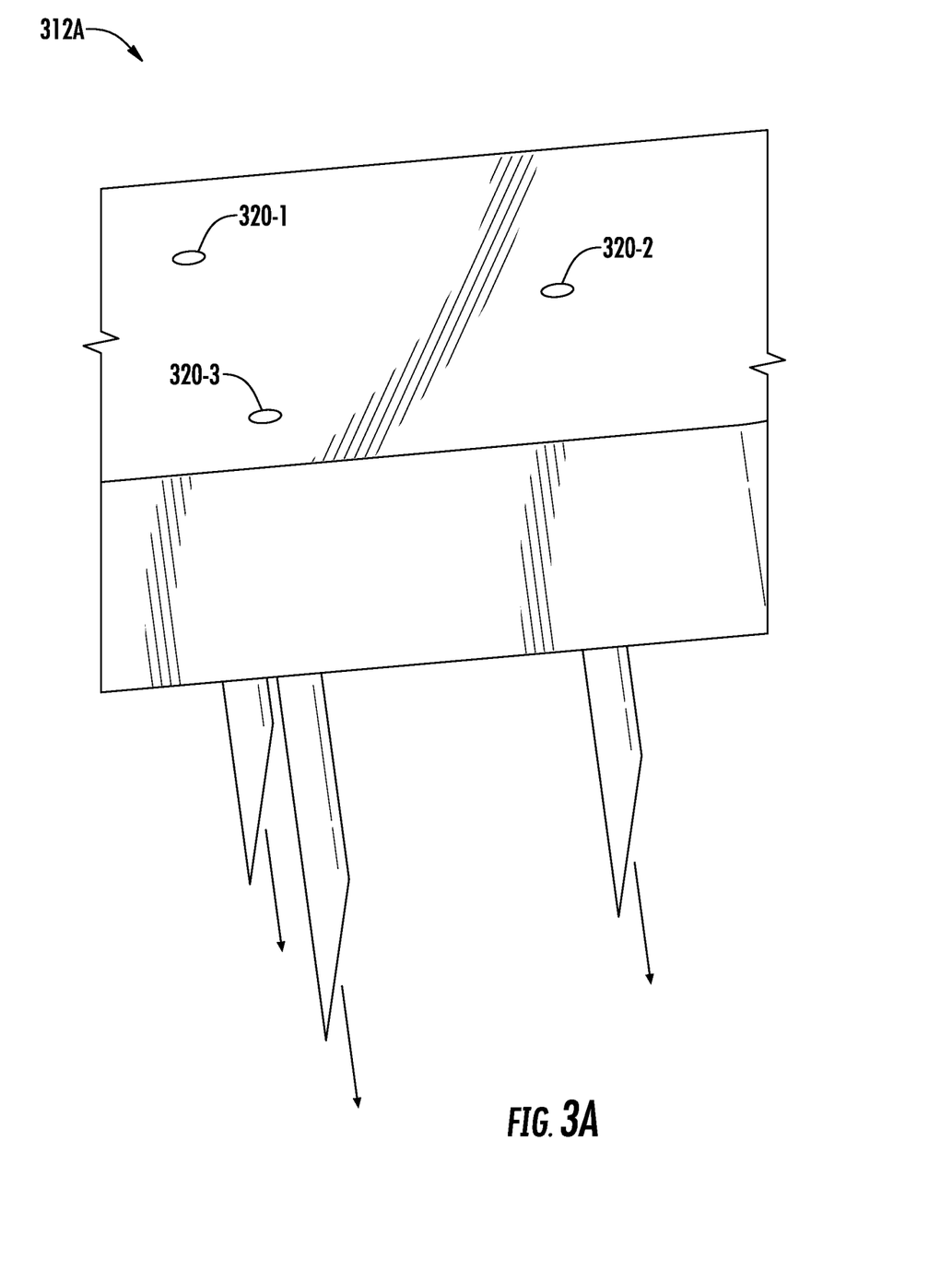
FIGS. 3A and 3B illustrate various aspects of a crossmember according to one or more embodiments of the present disclosure.
Figure 3B:
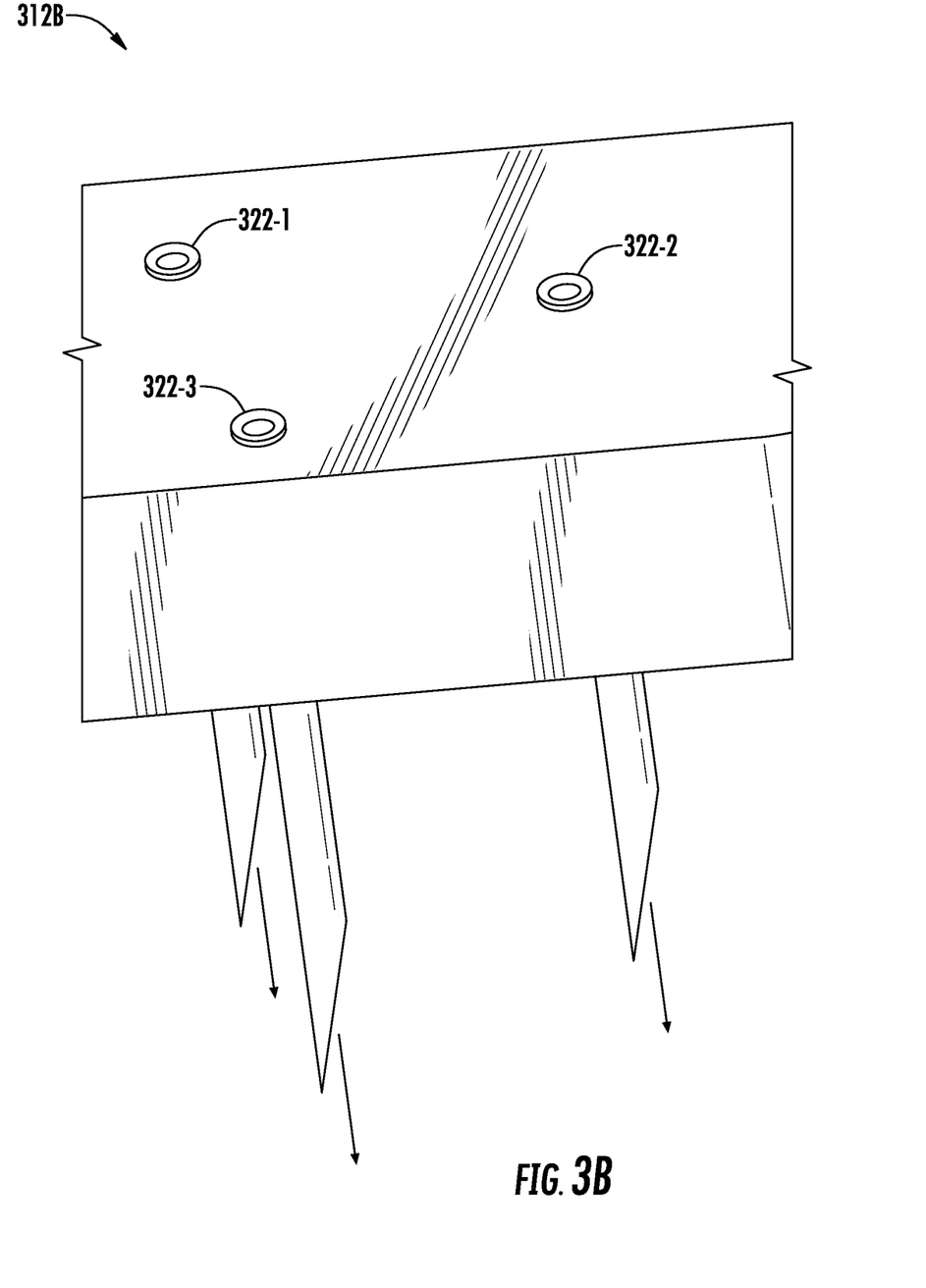

FIGS. 3A and 3B illustrate various aspects of crossmembers 312A, 312B according to one or more embodiments of the present disclosure. More specifically, FIG. 3A illustrates a crossmember 312A with through holes 320-1, 320-2, 320-3 (or through holes 320) and FIG. 3B illustrates a crossmember 312B with through holes (not labeled) that include connectors 322-1, 322-2, 322-3 (or connectors 322). In some embodiments, FIGS. 3A and/or 3B may include one or more components that are the same or similar to one or more other components of the present disclosure. Further, one or more components of FIGS. 3A and/or 3B, or aspects thereof, may be incorporated into other embodiments of the present disclosure without departing from the scope of this disclosure. For example, crossmember 312A or cross member 312B may be incorporated into fluid container adapter 102 as crossmember 112. The through holes of crossmembers 312A, 312B (or crossmembers 312) may extend from one side of the crossmembers 312 to the other side. In various embodiments of the present disclosure, the through holes may be in fluid communication with lumens of the penetration members. Embodiments are not limited in this context.

In various embodiments, tubes of an endoscopic system may utilize the through holes 320 and/or connectors 322 to gain access to the contents of a fluid container. For example, each of the through holes 320 of crossmember 312A may be sized such that tubes can extend into the interior of a fluid container by being passed though the through holes and the lumens of the penetration members. In another example, tubes may connect to the through holes of crossmember 312B via connectors 322. In some embodiments, the through holes 320 and/or connectors 322 may form a fluid tight seal with the exterior of tubes. In some such embodiments, the through holes 320 and/or connectors 322 may maintain a slidable seal with the exterior of a tube. For instance, each of through holes 320 and/or connectors 322 may maintain a fluid seal with the exterior of a tube as the tube is inserted through and into the interior of a fluid container. In various embodiments, the through holes 320 and/or connectors 322 may include one or more threaded portions. For instance, connectors 322 may be attached to corresponding through holes via corresponding threads. In other embodiments, a crossmember may include one or more internal channels with bends and/or corners to enable fluid communication to be established between the lumen of a penetration member and a tube. For example, the lumen of the penetration member may be placed in fluid communication with a tube connected to the frontside (i.e., side facing out of the page) via an internal channel. In some embodiments, a crossmember may include a manifold. For instance, the crossmember may include a branching internal channel that enables multiple penetration members to be placed in fluid communication with a single tube As will be described in more detail below, in many embodiments, the number of through holes and/or connectors may not directly correspond to the number of penetration members. For example, different endoscopic systems may require different numbers of tubes in fluid communication with the interior of a fluid container. Accordingly, one or more through holes may be blocked or unblocked and/or one or more penetration members may be removed or added to accommodate different endoscopic systems or different configuration of an endoscopic system. In other words, the crossmembers 312 can be adapted to different hose configurations and/or hose sets. Further, different types of penetration members may be used in conjunction.

Figure 4:
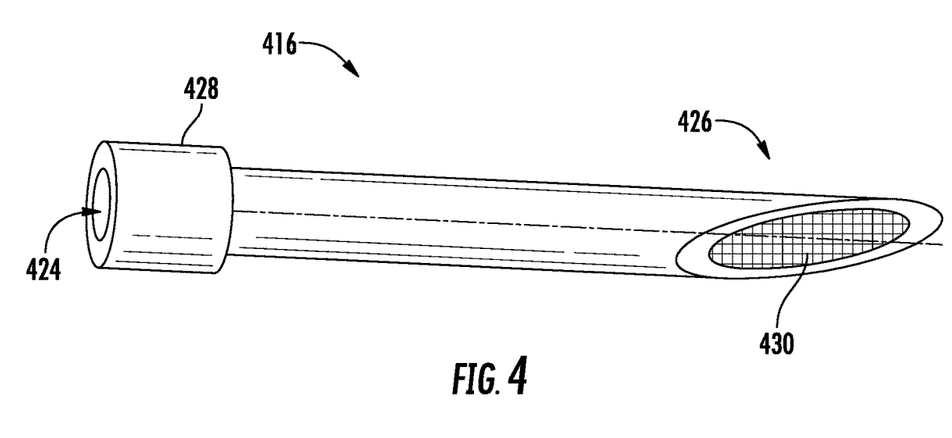
FIG. 4 illustrates various aspects of a penetration member according to one or more embodiments of the present disclosure.

FIG. 4 illustrates various aspects of a penetration member 416 according to one or more embodiments of the present disclosure. In some embodiments, FIG. 4 may include one or more components that are the same or similar to one or more other components of the present disclosure. Further, one or more components of FIG. 4, or aspects thereof, may be incorporated into other embodiments of the present disclosure without departing from the scope of this disclosure. For example, penetration member 416 may be incorporated into fluid container adapter 102 as one or more of penetration members 116. In the illustrated embodiment, penetration member 416 includes a lumen 424, a penetrator portion 426, a connector portion 428, and a filter screen 430. In one or more embodiments of the present disclosure, penetration member 416 may be utilized to gain access to the interior of a fluid container (e.g., fluid container 218). In various embodiments, the contents of the fluid container may be removed via lumen 424 or a tube inserted through lumen 424. Embodiments are not limited in this context.

The connector portion 428 may enable the penetration member 416 to be selectively coupled with a crossmember (e.g., crossmember 112). For example, connector portion 428 may include external threads that can couple with internal threads of a through hole (e.g., through hole 320-1). In some embodiments, connector portion 428 may enable the penetration member 416 to be selectively coupled with a tube. The penetrator portion 426 may enable the penetration member 416 to puncture a fluid container (e.g., fluid container 218) and place the lumen 424 in fluid communication with the contents of the fluid container. In one or more embodiments, the penetration member 416 may include a rigid tube. In various embodiments, the filter screen 430 may prevent particulates from entering the lumen 424. For example, filter screen 430 may reduce or minimize particulates from a fluid container generated by puncturing the fluid container from entering the lumen 424.

In several embodiments, a tube may be inserted through penetration member 416 to access and/or remove contents from a fluid container. In several such embodiments, filter screen 430 may be coupled to a distal end of the tube. In some embodiments, the tube may include a sealing portion configured to create a seal with an opening created by the penetration member and/or with the lumen 424. In various embodiments, the penetration member and/or a tube may be fed to the bottom of a fluid container in order to retrieve contents of the fluid container.

Figure 5:
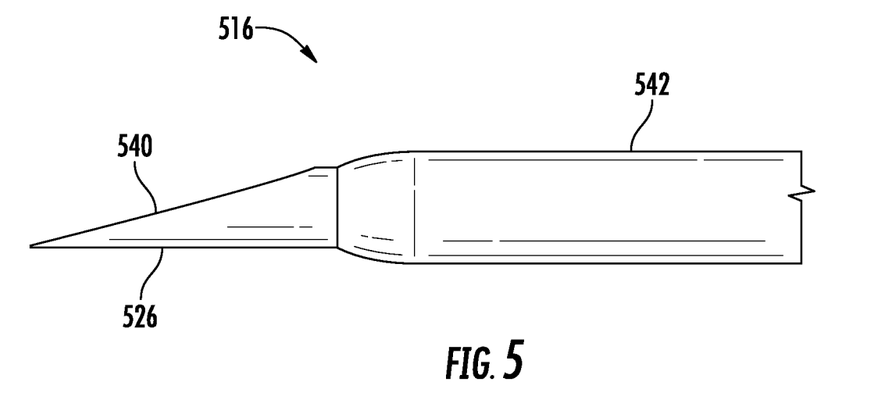
FIG. 5 illustrates various aspects of a penetration member according to one or more embodiments of the present disclosure.

FIG. 5 illustrates various aspects of a penetration member 516 according to one or more embodiments of the present disclosure. In some embodiments, FIG. 5 may include one or more components that are the same or similar to one or more other components of the present disclosure. Further, one or more components of FIG. 5, or aspects thereof, may be incorporated into other embodiments of the present disclosure without departing from the scope of this disclosure. For example, penetration member 516 may be incorporated into fluid container adapter 102 as one or more of penetration members 116. In the illustrated embodiment, penetration member 516 includes a penetrator portion 526 with a beveled tip 540 and a sealing portion 542. In several embodiments of the present disclosure, the penetrator portion 526 may be utilized to puncture a fluid container and/or the sealing portion 542 may be utilized to create a seal with the fluid container. Embodiments are not limited in this context.

The beveled tip 540 of the penetrator portion 526 may enable the penetration member 516 to puncture a fluid container (e.g., fluid container 218) to gain access to the contents of the fluid container. The sealing portion 542 may be configured to create a seal between an exterior of the penetration member 516 and the fluid container. In many embodiments, the sealing portion 542 (or any sealing component herein) may comprise a synthetic rubber or elastomer. For example, the sealing portion 542 may include an elastomer (e.g., silicone) and/or low durometer material (e.g., 20-70 Shore A) disposed about a circumference of the external surface of the penetration member 516. In various embodiments, the sealing portion 542 may conform to the shape of the hole in the fluid container generated by the penetrator portion 526.

In various embodiments, a tube may be inserted through penetration member 516 and fed into a fluid container (e.g., to the bottom). In various such embodiments, the tube may include a sealing portion that creates a seal with the wall of a lumen extending through penetration member 516. In some embodiments, penetration member 516 may be coupled to the end of a tube. In some such embodiments, the tube may include a sealing portion that creates a seal with the opening in a fluid container created by the penetration member 516. In further such embodiments, the sealing portion of the tube may be able to slide along at least a portion of the length of the tube while maintaining a seal.

Figure 6:
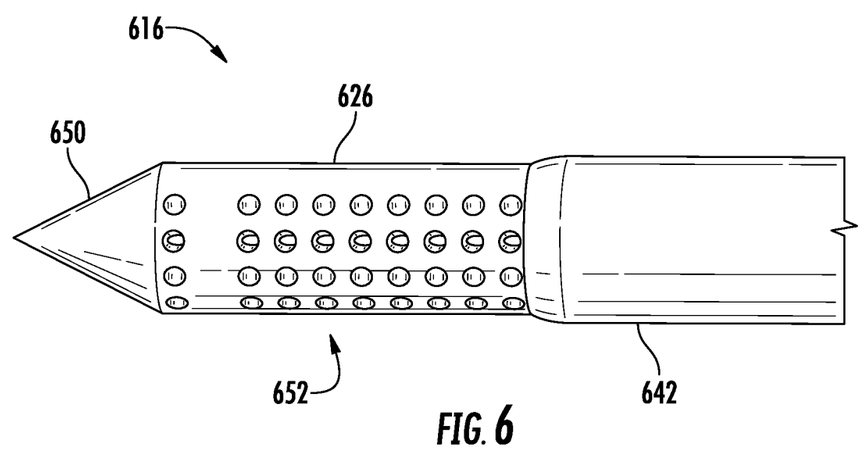
FIG. 6 illustrates various aspects of a penetration member according to one or more embodiments of the present disclosure.

FIG. 6 illustrates various aspects of a penetration member 616 according to one or more embodiments of the present disclosure. In some embodiments, FIG. 6 may include one or more components that are the same or similar to one or more other components of the present disclosure. Further, one or more components of FIG. 6, or aspects thereof, may be incorporated into other embodiments of the present disclosure without departing from the scope of this disclosure. For example, penetration member 616 may be incorporated into fluid container adapter 102 as one or more of penetration members 116. In the illustrated embodiment, penetration member 616 includes a sealing portion 642 and a penetrator portion 626 with conical tip 650 and radial holes 652 (or radial openings 652). In many embodiments of the present disclosure, the conical tip 630 of penetrator portion 626 may be utilized to puncture a fluid container, the radial holes 652 of penetrator portion 626 may act as a filter, and/or the sealing portion 642 may be utilized to create a seal with the fluid container. Embodiments are not limited in this context.

The conical tip 650 of the penetrator portion 626 may enable the penetration member 616 to puncture a fluid container (e.g., fluid container 218) to gain access to the contents of the fluid container. Further, the radial holes 652 may allow fluid to enter the lumen of penetration member 616 while preventing particulates from entering the lumen of penetration member 616. For example, radial holes 652 may prevent particulates generated by puncturing the fluid container and/or already present in the fluid container from entering the lumen of penetration member 616. Other designs and/or shapes may be used in place of radial holes 652 to prevent particulates from entering the lumen of penetration member 616. For example, slots, screens, grids, and the like may be utilized in place of radial holes 652 to prevent particulates from entering the lumen of penetration member 616. Sealing portion 642 may be the same or similar to sealing portion 542. Accordingly, sealing portion 642 may be configured to create a seal between an exterior of the penetration member 616 and a fluid container punctured by penetrator portion 626.

In some embodiments, penetration member 616 may be coupled to the end of a tube. In some such embodiments, the tube may include a sealing portion that creates a seal with the opening in a fluid container created by the penetration member 616. In further such embodiments, the sealing portion of the tube may be able to slide along at least a portion of the length of the tube while maintaining a seal. In some embodiments, a tube may include a sealing portion that creates a seal with the wall of a lumen extending through penetration member 616.

Figure 7:
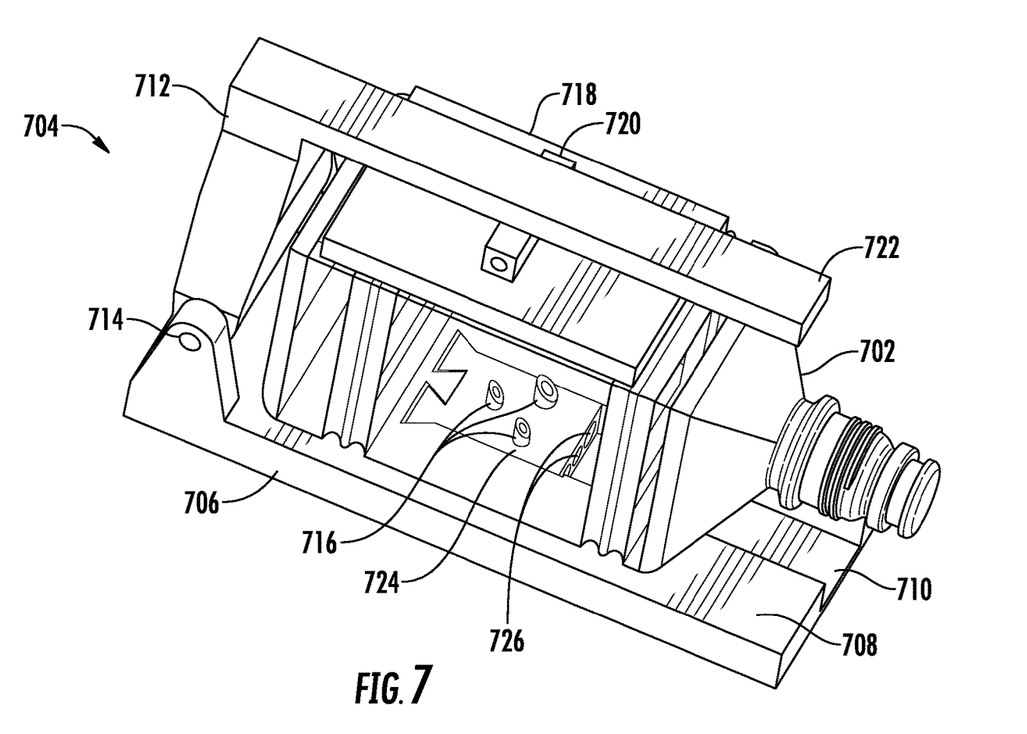
FIG. 7 illustrates an exemplary fluid container adapter in conjunction with a fluid container according to one or more embodiments of the present disclosure.

FIG. 7 illustrates a fluid container adapter 704 in conjunction with a fluid container 702 according to one or more embodiments of the present disclosure. In some embodiments, FIG. 7 may include one or more components that are the same or similar to one or more other components of the present disclosure. For example, penetration members 716 may be the same or similar to one or more of penetration members 416, 516, 616. Further, one or more components of FIG. 7, or aspects thereof, may be incorporated into other embodiments of the present disclosure without departing from the scope of this disclosure. For example, channel 710 may be incorporated into crossmember 112 such that cartridge 724 could be used in conjunction with fluid container adapter 102. In the illustrated embodiment, fluid container adapter 704 includes a platform 706, an arm 712 connected to the platform 706 via hinge 714, contact member 718 connected to arm 712 via hinge 720, and cartridge 724 received by a channel 710 in a support surface 708 of platform 706. Embodiments are not limited in this context.

In one or more embodiments of the present disclosure, the components of fluid container adapter 704 may interoperate to couple with fluid container 702 and enable an endoscopic system to access the contents of the fluid container 702. In many embodiments, the cartridge 724 may be loaded into the platform 706 via channel 710. In many such embodiments, the cartridge 724 and the channel 710 may include one or more interlocking features (e.g., a dove tail configuration). In some embodiments, the cartridge 724 may be loaded from a top end of the channel 710. In some such embodiments, the channel 710 may include a receiving groove. In various embodiments, the channel 710 may be configured such that the cartridge 724 could be loaded from the bottom or either side. In several embodiments, the cartridge 724 may include one or more penetration members 716 and one or more ports 726. In many embodiments, the channel 710 may provide a passageway for tubes that are coupled to ports 726. In one embodiment, the contact member 718 may include a channel in place of the channel 710 in support surface 708. In such embodiments, the cartridge 724 may be loaded into the contact member 718. The channel 710 and cartridge 724 configuration could be incorporated to other embodiments of the current disclosure without departing from the scope of this disclosure. For example, channel 710 may be incorporated into support surface 106 such that cartridge 724 could be used in conjunction with fluid container adapter 102.

When the fluid container 702 is loaded onto the support surface 708 of platform 706, the arm 712 may be pivoted via hinge 714 using handle 722. Pivoting of the arm 712 may cause contact member 718 to force fluid container 702 towards support surface 708 such that penetration members 716 puncture the fluid container 702. In several embodiments, handle 722 may be positioned such that a mechanical advantage is realized when pivoting of the arm 712 causes contact member 718 to force fluid container 702 towards support surface 708. For example, handle 722 may be positioned at an opposite end of the arm 712 as the hinge 714. In many embodiments, hinge 720 may enable contact member 718 to pivot and apply uniform pressure to the surface of fluid container 702.

In some embodiments, the cartridge 724 may be reconfigurable and/or disposable. For example, one or more of the penetration members 716 may removably couple to the cartridge 724. For instance, penetration members 716 may thread into the cartridge 724. In various embodiments, tubing may extend from each of the ports 726. In several embodiments, tubing may removably couple to the ports 726 of the cartridge 724. In many embodiments, different penetration members 716 may be configured to extend further into the fluid container 702 than other penetration members 716. In several embodiments, the cartridge 724 may include one or more ports 726 and one or more penetration members 716.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method of the present disclosure without departing from the concept, spirit and scope of the disclosure. All such similar substitutes and modifications apparent to those skilled in the art are deemed to be within the spirit, scope and concept of the disclosure as defined by the appended claims.

What is claimed is:

1. An adapter for fluid containers, comprising:
   a platform including first and second rails extending from the platform, the first and second rails extending substantially parallel to each other; and
   a crossmember slidably attached to the first and second rails such that the platform and the crossmember are substantially parallel to each other, wherein the platform, the crossmember, and the first and second rails are adjustable for receiving a fluid container, wherein the crossmember includes one or more penetration members extending from the crossmember towards the platform, each of the one or more penetration members comprising a lumen and a penetrator portion with an opening to the lumen, the penetrator portion configured for piercing the fluid container when the crossmember is moved towards the platform along the first and second rails.

2. The adapter of claim 1, wherein the opening of the penetrator portion of at least one of the one or more penetration members comprises a plurality of radial openings to the lumen.

3. The adapter of claim 1, wherein the penetrator portion of at least one of the one or more penetration members comprises a conical point.

4. The adapter of claim 1, wherein the penetrator portion of at least one of the one or more penetration members comprises a beveled tip.

5. The adapter of claim 1, wherein at least one of the one or more penetration members comprises a sealing portion, the sealing portion configured to create a seal between an exterior of the penetration member and the fluid container.

6. The adapter of claim 5, wherein the sealing portion comprises an elastomer disposed about a circumference of the exterior surface of the penetration member.

7. The adapter of claim 6, wherein the first rail comprises a first channel, the second rail comprises a second channel, and the crossmember comprises first and second pegs, the first peg extending into the first channel to slidably attach the first rail to the crossmember and the second peg extending into the second channel to slidably attach the second rail to the crossmember.

8. The adapter of claim 6, wherein the lumen and the opening of at least one of the one or more penetration members are configured to have a tube extended therethrough and into an interior of the fluid container after the fluid container is pierced with the penetrator portions of the one or more penetration members.

9. The adapter of claim 6, wherein the crossmember comprises a first side and a second side with a through hole extending from the first side to the second side, wherein at least one of the one or more penetration members extend from the first side and the through hole is in fluid communication with the lumen of the at least one penetration member.

10. The adapter of claim 6, wherein at least one of the one or more penetration members comprise a connector portion configured to couple to a tube and place the tube in fluid communication with the lumen of the at least one penetration member.

11. The adapter of claim 6, wherein the opening of at least one of the one or more penetration members comprises a filter screen.

12. The adapter of claim 6, wherein the one or more penetration members comprise a first penetration member and a second penetration member, and further comprising:
    a pressure source in fluid communication with the lumen of the second penetration member, wherein the pressure source is configured to introduce a first fluid into an interior of the fluid container to cause a second fluid to exit the interior of the fluid container via the lumen of the first penetration member.

13. The adapter of claim 12, wherein the first penetration member comprises a first sealing portion configured to create a seal between an exterior of the first penetration member and the fluid container, and the second penetration member comprises a second sealing portion configured to create a seal between an exterior of the second penetration member and the fluid container.

14. An apparatus, comprising:
    a platform comprising a support surface configured to support a fluid container;
    a first rail attached to the platform and extending from the support surface;
    a second rail attached to the platform and extending from the support surface parallel to the first rail;
    a crossmember comprising one or more mounts configured to connect to one or more penetration members, the crossmember slidably connected to the first rail and the second rail;
    and a penetration member connected to the crossmember via a mount of the one or more mounts and extending toward the support surface, the penetration member comprising a lumen and a penetrator portion with an opening to the lumen, the penetrator portion configured to puncture the fluid container supported by the support surface and place an interior of the fluid container in fluid communication with the lumen of the penetration member via the opening when the crossmember is slid toward the support surface along the first and second rails.

15. The apparatus of claim 14, comprising a lever configured to slide the crossmember toward the support surface along the first and second rails.

16. The apparatus of claim 14, wherein the opening comprises a filter screen.

17. A method, comprising:
    attaching a first rail and a second rail to a platform, the platform including a support surface configured to support a fluid container and the first and second rails extending substantially parallel to one another from the support surface; and slidably connecting a crossmember to the first rail and the second rail, the crossmember including one or more penetration members;

wherein the penetration member extends toward the support surface of the platform and includes a lumen and a penetrator portion with an opening to the lumen, the penetrator portion configured to puncture the fluid container supported by the support surface and place an interior of the fluid container in fluid communication with the lumen of the penetration member via the opening when the crossmember is slid toward the support surface along the first and second rails.

18. The method of claim 17, further comprising disposing an elastomer about an exterior circumference of the penetration member to form a sealing portion of the penetration member, the sealing portion configured to create a seal between the exterior of the penetration member and the fluid container when the interior of the fluid container is in fluid communication with the lumen of the penetration member.

19. The method of claim 17, further comprising pivotally attaching a lever to the crossmember, wherein activation of the lever is configured to force the crossmember toward the support surface.

20. The method of claim 19, further comprising extending the lever through a channel in the first rail or the second rail to configure the lever to force the crossmember toward the support surface.

* * * * *